United States Patent
Benesh

(10) Patent No.: US 7,137,471 B1
(45) Date of Patent: Nov. 21, 2006

(54) ALCOHOL AND DRUG SENSOR SYSTEM FOR VEHICLES

(76) Inventor: George Benesh, 35-36-88th St., Apt 3 DN, Jackson Heights, NY (US) 11372

( * ) Notice: Subject to any disclaimer, the term of this patent is extended or adjusted under 35 U.S.C. 154(b) by 397 days.

(21) Appl. No.: 10/665,674

(22) Filed: Sep. 18, 2003

Related U.S. Application Data

(60) Provisional application No. 60/411,580, filed on Sep. 18, 2002.

(51) Int. Cl.
*B60K 28/06* (2006.01)
(52) U.S. Cl. .............. 180/272; 180/272; 340/576; 702/183
(58) Field of Classification Search ............ 180/272, 180/287; 340/576; 702/183; *B60K 28/06*
See application file for complete search history.

(56) References Cited

U.S. PATENT DOCUMENTS

| 4,039,852 | A | * | 8/1977 | Miyamoto et al. ............ 307/32 |
| 5,531,225 | A | * | 7/1996 | Nawata et al. ............ 600/532 |
| 5,743,349 | A |   | 4/1998 | Steinberg |
| 5,969,615 | A |   | 10/1999 | Ivey, Jr. et al. |
| 6,167,746 | B1 |   | 1/2001 | Gammenthaler |
| 6,853,956 | B1 | * | 2/2005 | Ballard et al. ............ 702/183 |

* cited by examiner

*Primary Examiner*—Eric Culbreth

(57) ABSTRACT

An alcohol and drug sensor system for vehicles for preventing ignition of a vehicle engine by an intoxicated driver includes a gas chromatograph sensor operationally coupled to a sample collection tube. The sensor is operationally coupled to a microprocessor that prevents the ignition system of the vehicle from working until a breath sample is collected and the intoxicant content of the breath sample is determined to be below a pre-determined level.

8 Claims, 3 Drawing Sheets

ALCOHOL AND DRUG SENSOR SYSTEM FOR VEHICLES

CROSS REFERENCE TO RELATED APPLICATION

This application claims the benefit of U.S. Provisional Application No. 60/411,580, filed Sep. 18, 2002.

BACKGROUND OF THE INVENTION

1. Field of the Invention

The present invention relates to sensors and more particularly pertains to a new alcohol and drug sensor for vehicles for preventing ignition of a vehicle engine by an intoxicated driver.

2. Description of the Prior Art

The use of sensors for preventing intoxicated operation of a vehicle is known in the prior art. U.S. Pat. No. 5,743,349 describes a system for non-invasive measuring of blood alcohol using optical spectroscopic electromagnetic radiation. Another type of sensor used in restricting vehicle operation is U.S. Pat. No. 5,969,615 having a plurality of passageways positioned adjacent to the hand position of the driver to sample vapor emitted from the hands of the driver. U.S. Pat. No. 6,167,746 discloses an alcohol concentration sensing system that uses breath pressure measurement to control the volume of breath analyzed.

While these devices fulfill their respective, particular objectives and requirements, the need remains for a system that incorporates gas chromatography into the analysis of breath and processes the collected information to selectively activate a vehicle ignition system when the breath of the potential driver does not contain threshold levels of intoxicants.

SUMMARY OF THE INVENTION

The present invention generally comprises a gas chromatograph sensor operationally coupled to a sample collection tube. The sensor is operationally coupled to a microprocessor that prevents the ignition system of the vehicle from working until a breath sample is collected and the intoxicant content of the breath sample is determined to be below a pre-determined level.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
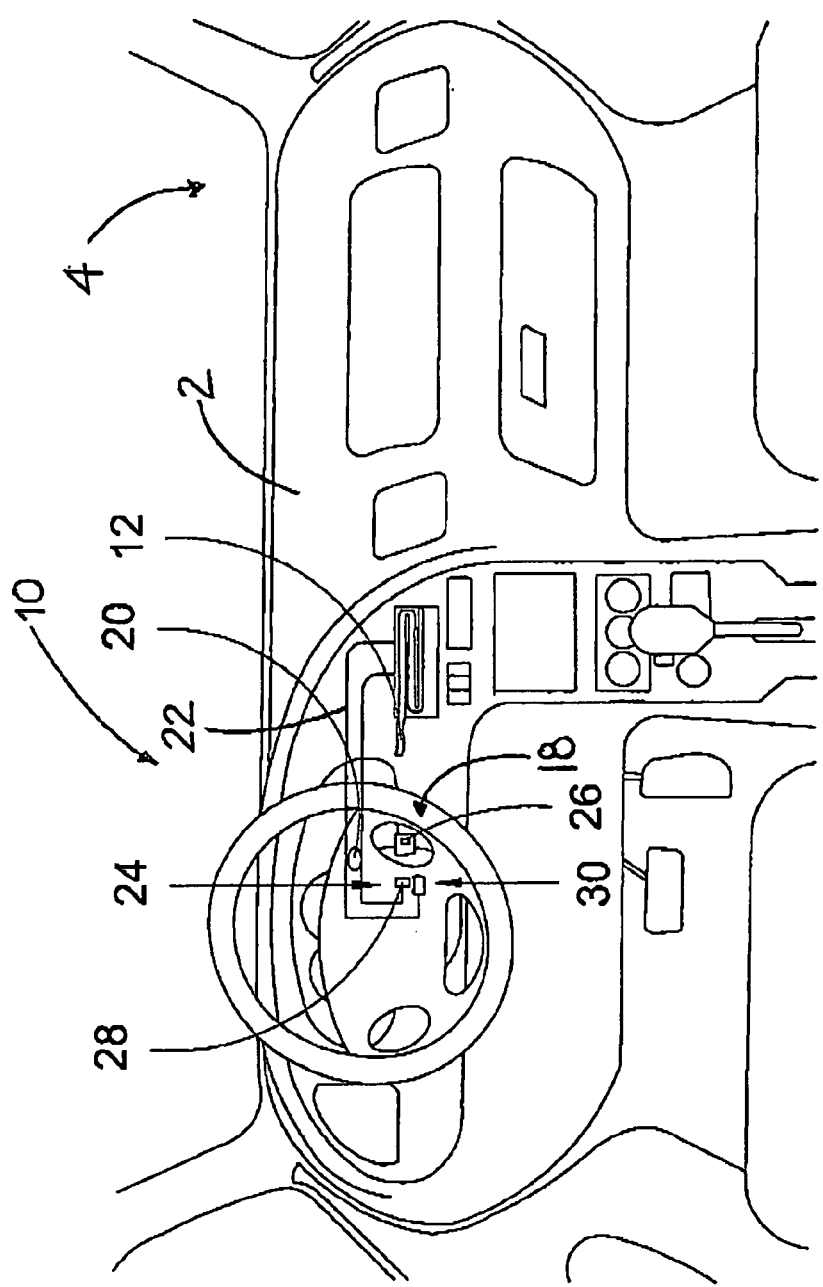
FIG. 1 is a schematic front view of a new alcohol and drug sensor system for vehicles according to the present invention.
Figure 2:
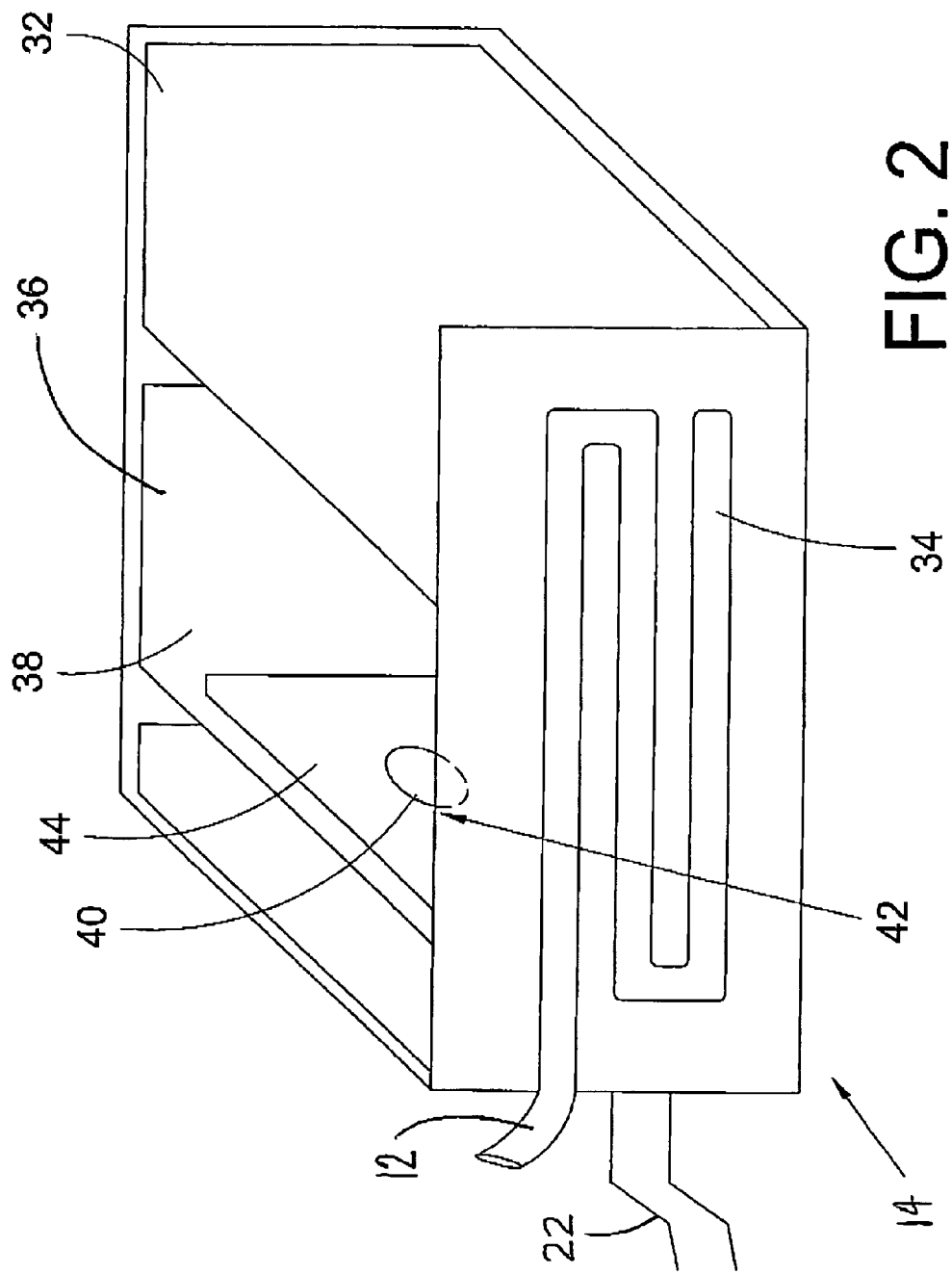
FIG. 2 is a perspective view of the present invention.
Figure 3:
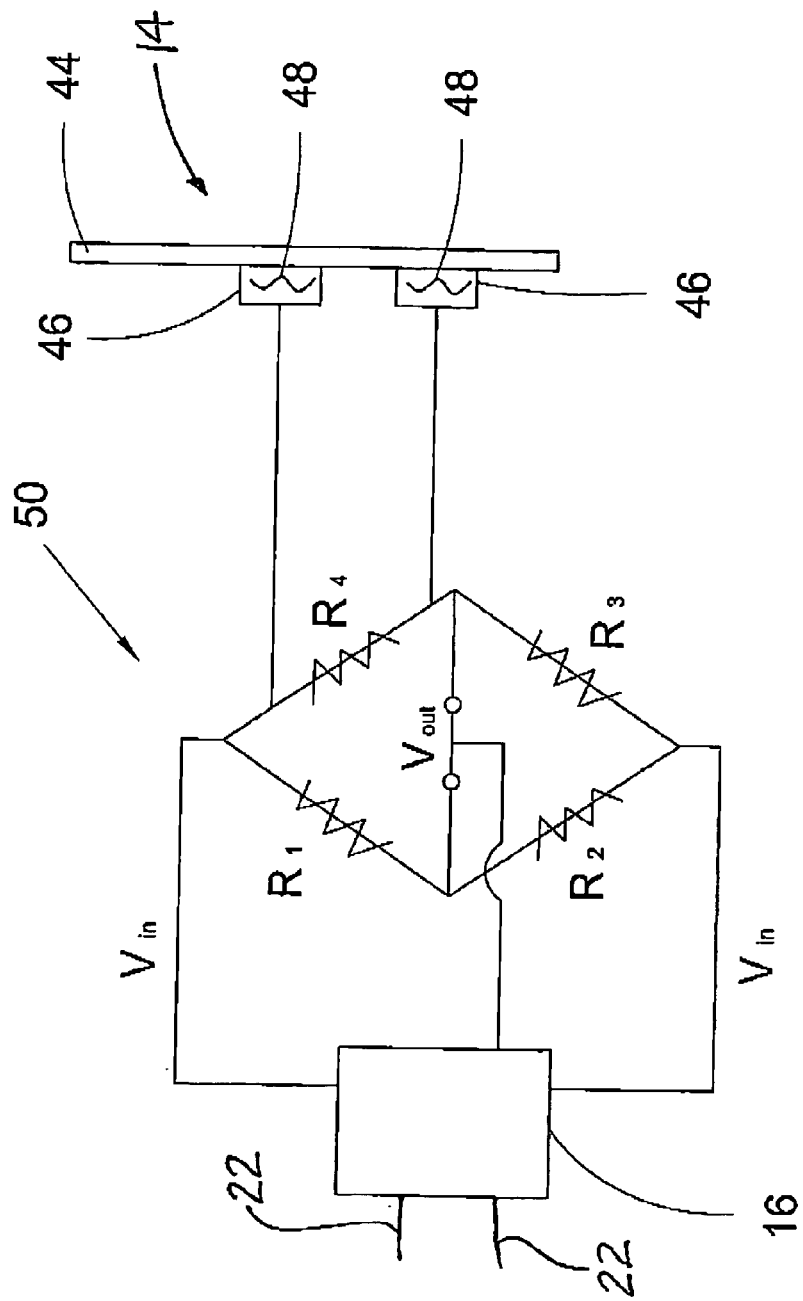
FIG. 3 is a representational side view of the silicon wafer thermal detectors and wheatstone bridge assembly of the sensor of the present invention.

With reference now to the drawings, and in particular to FIGS. 1 through 3 thereof, a new alcohol and drug sensor system for vehicles embodying the principles and concepts of the present invention and generally designated by the reference numeral 10 will be described.

As illustrated in FIGS. 1 through 3, the alcohol and drug sensor system for vehicles 10 generally comprises a main tube 12 extending from the dashboard 2 of a vehicle 4 or other structure near to the potential driver of the vehicle 4 such as the vehicle's frame, floor, seat or the like. The main tube 12 is connected to a sensor 14 for detecting the presence of intoxicants in the breath of a person blowing into the main tube 12. The sensor 14 is operationally coupled to a microprocessor 16. The ignition system 18 of the vehicle 4 is operationally coupled to the microprocessor 16 such that the ignition system 18 cannot be activated until a potential driver has blown into the main tube 12. If a level of intoxicants detected by the sensor 14 is over a pre-determined level, the microprocessor 16 will not activate the ignition system 18, thus preventing the vehicle 4 from being driven. If the level of intoxicants is below the pre-determined level, the microprocessor 16 activates a relay 20 to enable the ignition system 18 to permit the ignition system 18 to be used to start the engine of the vehicle 4. Most preferably, the microprocessor 16 is operationally coupled (by connections 22) to a locking means 24 for physically preventing turning of an ignition key 26. The means 24 may be a conventionally known physical lock such as a solenoid 28 engaging the ignition key assembly 30 to prevent rotation of the ignition key 26.

The sensor 14 uses gas chromatography. The components of the sensor 14 are a carrier-gas supply and flow controller 32, a sample inlet tube 34, a chromatographic column 36, and a column oven 38. A breath sample is injected into the sample inlet tube 34 when the potential driver blows into the main tube 12. The sample is channeled through the carrier gas supply and flow controller 32 (see FIG. 2) into the column oven 38 to heat the sample. The elements of the breath sample are then distinguished using the retention time within the column 36. The sample leaves the column 36 and moves through an opening or hole 40 in a resistance measuring means positioned adjacent to the column 36 for measuring the electrical resistance of a fluid passing through the hole 40. The sample moves through the hole 40 in the center 42 of a silicone wafer 44 of the resistance measuring means. Two thermal detectors 46 utilizing serpentine strands 48 of nickel wire with very low resistance are positioned near the hole 40 in the silicone wafer 44. The strands 48 of nickel wire are approximately 20 microns thick and one inch long. A wheatstone bridge 50 is attached to the detectors 46. When the elements of the breath sample pass through the hole 40, the resistance between the detectors 46 is measured. The changes in resistance are then used to determine the contents of the breath sample.

In use, the potential driver of the vehicle must blow into the main tube and wait briefly for the gas chromatograph analysis and subsequent activation of the ignition system of the vehicle.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An alcohol sensor system for vehicles comprising:
   a vehicle;
   a main tube coupled to said vehicle such that said main tube is accessible to a user while in a driver's position within said vehicle;
   a sensor assembly operationally coupled to said main tube for detecting intoxicants in a breath of said user when said user blows into said main tube;
   a microprocessor operationally coupled to said sensor assembly;
   an ignition system of said vehicle being operationally coupled to said microprocessor such that said ignition system cannot be activated until said user has blown into said main tube;
   wherein said microprocessor prevents activation of said ignition system when a level of intoxicants detected by said sensor assembly is over a pre-determined level;
   wherein said microprocessor activates a relay to enable said ignition system to permit said ignition system to be used to start said vehicle when said level of intoxicants detected by said sensor assembly is below said pre-determined level;
   wherein said sensor assembly uses gas chromatography to detect said level of intoxicants;
   wherein said sensor assembly comprises:
      a sample inlet tube environmentally coupled to said main tube;
      a carrier-gas supply flow controller coupled to said sample inlet tube for regulating flow of exhaled breath through said sensor assembly;
      a chromatographic column coupled to said carrier-gas supply flow controller, said chromatographic column having an exit;
      a resistance measuring means having an opening positioned adjacent to said exit for measuring electrical resistance of a fluid passing through said exit; and
      a column oven coupled to said chromatographic column for heating said exhaled breath as said exhaled breath passes into said chromatographic column whereby elements of said exhaled breath are separated by retention time within said chromatographic column before passing through said exit.

2. The alcohol sensor system for vehicles of claim 1, further comprising:
   a locking means for physically preventing turning of an ignition key; and
   wherein said microprocessor is operationally coupled to said locking means for physically preventing turning of said ignition key when said level of intoxicants detected by said sensor assembly is over a pre-determined level.

3. The alcohol sensor system of claim 1, wherein said resistance measuring means comprises:
   a silicone wafer defining said opening of said resistance measuring means;
   a pair of thermal detectors each having a plurality of serpentine strands of nickel wire, said thermal detectors being positioned proximate said opening; and
   a wheatstone bridge being attached to said thermal detectors.

4. The alcohol sensor system of claim 3 wherein each of said strands of nickel wire is approximately 20 microns thick and approximately one inch long.

5. An alcohol sensor system for vehicles comprising:
   a main tube for coupling to a vehicle such that said main tube is accessible to a user while the user is seated in a driver's position in the vehicle;
   a sensor assembly operationally coupled to said main tube for detecting intoxicants in a breath of said user when said user blows into said main tube, said sensor assembly using gas chromatography to detect said level of intoxicants;
   a microprocessor operationally coupled to said sensor assembly, said microprocessor being configured for coupling to an ignition system of the vehicle such that the ignition system cannot be activated until the user has blown into said main tube, said microprocessor being further configured to prevent activation of the ignition system when a level of intoxicants detected by said sensor assembly is greater than a pre-determined level, said microprocessor being further configured to activate a relay to enable the ignition system to be used to start an engine of the vehicle when said level of intoxicants detected by said sensor assembly is below said pre-determined level;
   wherein said sensor assembly comprises:
      a sample inlet tube environmentally coupled to said main tube;
      a carrier-gas supply flow controller coupled to said sample inlet tube for regulating flow of exhaled breath through said sensor assembly;
      a chromatographic column coupled to said carrier-gas supply flow controller, said chromatographic column having an exit;
      a resistance measuring means having an opening positioned adjacent to said exit for measuring electrical resistance of a fluid passing through said exit; and
      a column oven coupled to said chromatographic column for heating said exhaled breath as said exhaled breath passes into said chromatographic column whereby elements of said exhaled breath are separated by retention time within said chromatographic column before passing through said exit.

6. The alcohol sensor system for vehicles of claim 5, further comprising:
   a locking means for physically preventing turning of an ignition key of the ignition system of the vehicle; and
   wherein said microprocessor is operationally coupled to said locking means for selectively causing said locking mean physically preventing turning of said ignition key when said level of intoxicants detected by said sensor assembly is over a pre-determined level.

7. The alcohol sensor system of claim 5, wherein said resistance measuring means comprises:
   a silicone wafer defining said opening of said resistance measuring means;

a pair of thermal detectors each having a plurality of serpentine strands of nickel wire, said thermal detectors being positioned proximate said opening; and a wheatstone bridge being attached to said thermal detectors.

8. The alcohol sensor system of claim 7 wherein each of said strands of nickel wire is approximately 20 microns thick and approximately one inch long.

\* \* \* \* \*